United States Patent [19]

Confalone et al.

[11] 4,029,647

[45] June 14, 1977

[54] SYNTHESIS OF BIOTIN

[75] Inventors: Pasquale Nicholas Confalone, Bloomfield; Milan Radoje Uskokovic, Upper Montclair; Giacomo Pizzolato, Belleville, all of N.J.

[73] Assignee: Hoffmann-La Roche Inc., Nutley, N.J.

[22] Filed: May 12, 1976

[21] Appl. No.: 685,835

Related U.S. Application Data

[62] Division of Ser. No. 421,460, Dec. 3, 1973, Pat. No. 3,978,084.

[52] U.S. Cl. .................... 260/239.3 B; 260/309.7; 260/332.2 A; 260/332.2 C

[51] Int. Cl.$^2$ ...................... C07D 493/04
[58] Field of Search .......................... 260/239.3 B

[56] References Cited

OTHER PUBLICATIONS

Fabrichnii et al., "Zhur. Obsh. Khim.," vol. 31, No. 4 (1961).

*Primary Examiner*—Henry R. Jiles
*Assistant Examiner*—Robert T. Bond
*Attorney, Agent, or Firm*—Samuel L. Welt; Bernard S. Leon; Richard A. Gaither

[57] ABSTRACT

Synthesis of biotin from 4-carbomethoxy-2-(4,5-dihydrothiophen-3(2H)-one)-valeric acid methyl ester, and thiophene intermediates in this synthesis.

2 Claims, No Drawings

SYNTHESIS OF BIOTIN

This is a division of application Ser. No. 421,460 filed Dec. 3, 1973, entitled "Synthesis of Biotin", now U.S. Pat. No. 3,978,084.

SUMMARY OF THE INVENTION

This invention is directed to a process for selectively synthesizing biotin, which has the structural formula:

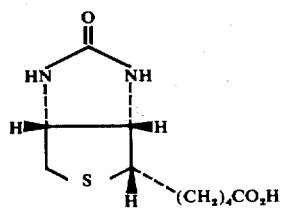

from a 4,5-dihydrothiophene compound of the formula:

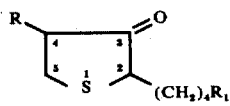

wherein R and $R_1$ are carboxy or carboxy protected with a group convertible thereto by hydrolysis.

By means of this process, biotin can be economically produced in high yields from the 4,5-dihydrothiophene of formula I.

DETAILED DESCRIPTION OF THE INVENTION

As used throughout this application, the term "carboxy protected with a group convertible thereto by hydrolysis" comprehends any conventional organic acid protecting group which can be removed by hydrolysis. The preferred organic acid protecting groups are the esters. Any conventional ester that can be hydrolyzed to yield the acid can be utilized as the protecting group. Exemplary esters useful for this purpose are the lower alkyl esters, particularly methyl and ethyl esters, the aryl esters, particularly phenyl ester, and the aryl lower alkyl esters, particularly benzyl ester.

As also used throughout this application, the term "hydrocarbyl" denotes a monovalent substituent consisting solely of carbon and hydrogen. The term "aliphatic" with reference to hydrocarbyl denotes straight chain and branched chain groups of 1 to 20 carbon atoms, which are saturated or which contain one or more olefinic and/or acetylenic carbon to carbon bonds but which contain no aromatic unsaturation, such as methyl, ethyl, allyl, propargyl, hexenyl and decyl. The term "cycloaliphatic" with reference to hydrocarbyl denotes mononuclear groups of 3 to 7 carbon atoms and polynuclear groups of 7 to 17 carbon atoms, which are saturated or which contain one or more olefinic and/or acetylenic carbon to carbon bonds but which contain no aromatic unsaturation and which can contain one or more aliphatic hydrocarbyl moieties, such as menthyl, bornyl and cholesteryl.

As further used throughout this application, the term "lower alkyl" denotes straight chain and branched chain, saturated aliphatic hydrocarbyl groups having from 1 to 8 carbon atoms, such as methyl, ethyl and propyl, preferably methyl. As also used herein, the term "aryl" signifies mononuclear aromatic hydrocarbyl groups of 6 to 13 carbon atoms, such as phenyl and tolyl, which can be unsubstituted or substituted in one or more positions with a lower alkylenedioxy, a halogen, a nitro, a lower alkyl or a lower alkoxy sustituents, and polynuclear aryl groups of 10 to 17 carbon atoms, such as naphthyl, anthryl, phenanthryl and azulyl, which can be substituted with one or more of the aforementioned groups. The preferred aryl groups are the substituted and unsubstituted mononuclear aryl groups, particularly phenyl. As further used herein, the term "aryl lower alkyl" comprehends groups wherein "aryl" and "lower alkyl" are as defined above, particularly benzyl. As still further used herein, the term "lower alkoxy" comprehends groups having from 1 to 7 carbon atoms such as methoxy and ethoxy. Also herein, the term "halogen" or "halo", unless otherwise stated, comprehends fluorine, chlorine, bromine and iodine. Further herein, the term "lower alkylenedioxy" comprehends groups having 1 to 4 carbon atoms, such as methylenedioxy and ethylenedioxy. Still further herein, the terms "loweralkylamino", "arylamino" and "arylloweralkylamino" comprehend groups wherein "aryl" and "lower alkyl" are as defined above.

As still further used throughout this application, in the pictorial representations of the compounds of this application, a thickened tapered line (—◀) indicates a substituent which is in the β-orientation (above the plane of the molecule), a dotted line (---) indicates a subsituent which is in the α-orientation (below the plane of the molecule) and a wavy line (∼) indicates a substituent which is in either the α- or β-orientation. It is to be undersood that the pictorial representations of the compounds given throughout the specification are set forth for convenience and are to be construed as inclusive of other forms including enantiomers and racemates and are not to be construed as limited to the particular form shown, unless otherwise expressly stated.

In accordance with this invention, biotin is obtained by first converting the 4,5-dihydrothiophene of formula I to an oxime of the formula:

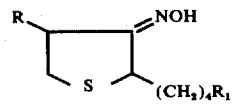

wherein R and $R_1$ are as above.

Any conventional mehod of preparing an oxime from a keto compound can be used to convert the 4,5-dihydrothiophene of formula I to the oxime of formula II. Preferaly, the 4,5-dihydorthiophene of formula I is treated with a hydroxylamine hydrohalide, preferably hydroxylamine hydrochloride, in a nitrogen-containing base. In carrying out this reaction, any conventional nitrogen-containing base can be utilized. The preferred nitrogen-containing bases are the amines. Among the amines which can be utilized are the primary amines, such as the loweralkylamines, particularly methylamine, ethylamine, and aniline; the secondary amines, such as the diloweralkylamines, particularly dimethylamine and diethylamine, and pyrrole; and the tertiary amines, such as the triloweralkylamines, particularly trimethylamine and triethylamine, pyridine and picoline. Also, in carrying out this reaciton with a hydroxylamine hydrohalide, temperature and pressure are not critical, and the reaction can be suitably carried out at from room temperature to reflux and at atmospheric pressure. Preferably, this reaction is carried out at room temperature (about 22° C.). Further, this reaction can be carried out in an inert organic solvent. In this reaction any conventional inert organic solvent can be utilized, such as the aliphatic or aromatic hydrocarbons, as for example n-hexane or benzene. Preferably, this reaction is carried out in an excess of the nitrogen-containing base, which serves as the solvent medium.

The oxime of formula II is then converted to an amine of the formula:

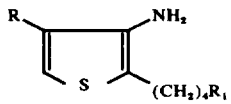

III wherein R and $R_1$ are as above.

This reaction is suitably carried out by treating the oxime of formula II with a hydrohalide in an inert, organic solvent under substantially anhydrous conditions. This reaction can be carried out in a conventional manner, preferably by treating the oxime of formula II with hydrogen chloride. In carrying out this reaction, any conventional inert organic solvent can be utilized. The preferred inert organic solvents are the ethers, particularly the dilower alkyl ethers, such as diethyl ether, and the cyclic ethers, such as tetrahydrofuran and dioxane. In carrying out this reaction, temperature and pressure are not critical, and this reaction can be suitably carried out at from 0° C. to about 70° C. and at atmospheric pressure. Preferably, this reaction is carried out at room temperature.

In carrying out the foregoing steps for converting the 4,5-dihydrothiophene of formula I to the amine of formula III, it is preferred that at least one and particularly that both of R and $R_1$ be carboxy protected with a group convertible thereto by hydrolysis, especially a lower alkyl ester group, particularly a methyl ester group. In accordance with this preferred aspect of the process of this application, the amine of formula III, wherein R and/or $R_1$ are carboxy protected with a group convertible thereto by hydrolysis, is then converted to an amino acid of the formula:

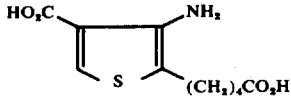

IV.

In carrying out this reaction, any conventional method of basic hydrolysis can be utilized. This hydrolysis can be suitably carried out in a conventional inert organic solvent. The preferred solvents are the lower alkanols, particularly methanol and ethanol, and the aqueous ether solvents, preferably the aqueous dilower alkyl ethers, particularly diethyl ether, and the aqueous cyclic ethers, particularly tetrahydrofuran and dioxane. In this reaction, any conventional base can be utilized. Among the preferred bases are the alkali metal hydroxides, such as sodium, potassium and lithium hydroxide, and the alkaline earth metal hydroxides, such as calcium and magnesium hydroxide, especially the alkali metal hydroxides. In this hydrolysis, temperature and pressure are not critical, and this reaction can be suitably carried out at from about 0° C. to about 100° C. and at atmospheric pressure. Preferably, this reaction is carried out at reflux, especially at about 70° C.

The amino acid of formula IV is then converted to a lactam of the formula:

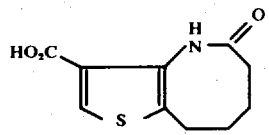

V.

The lactam of formula V can be obtained from the amino acid of formula IV in a conventional manner. Preferably, this reaction is carried out by heating the amino acid of formula IV in an inert organic solvent to a temperature of from about 80° C. to about 200° C., while removing the water formed in the reaction. In carrying out this reaction, any conventional inert organic solvent which has a boiling point above about 80° C. can be utilized. Preferred inert organic solvents include the aromatic hydrocarbons, such as benzene, xylene, and toluene. In carrying out this reaction, particular temperatures and pressures are not critical, and this reaction can be suitably carried out at about 100° C. and atmospheric pressure.

The lactam of formula V can also be obtained from an amine of formula III, wherein $R_1$ is carboxy and R is carboxy protected with a group convertible thereto by hydrolysis, i.e., a compound of the formula:

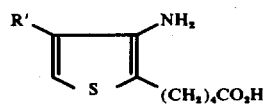

III-A wherein R' is carboxy protected with a group convertible thereto by hydrolysis;
by first converting the compound of formula III-A to a lactam of the formula:

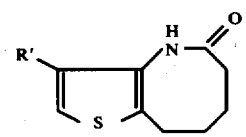

VI wherein R' is as above;
and then hydrolyzing the lactam of formula VI. In converting the compound of formula III-A to a lactam of formula VI and then hydrolyzing the lactam of formula VI to form the lactam of formula V, any conventional method for converting an amino acid to a lactam and for carrying out the basis hydrolysis of an ester can be utilized. Preferably, the procedure set forth above for forming the lactam of formula V from the amino acid of formula IV and for hydrolyzing the amine of formula III to form the amino acid of formula IV is utilized.

In accordance with this application, it is preferred to obtain the lactam of formula V from the amine of formula III by first hydrolyzing the amine of formula III to form the amino acid of formula IV and then converting the amino acid of formula IV to the lactam of formula V rather than by forming the lactam of formula VI from the compound of formula III-A and then hydrolyzing the resulting lactam of formula VI.

The lactam of formula V is then converted to mixed anhydride of the formula:

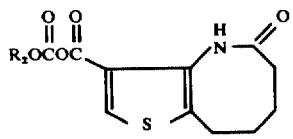

VII wherein $R_2$ is lower alkyl or phenyl;
which, in turn, is converted to an imido compound of the formula:

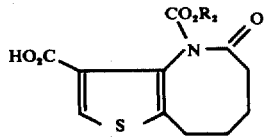

VIII wherein $R_2$ is as above;
and which, in turn, is converted to an imido-anhydride of the formula:

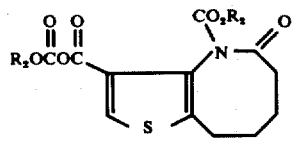

IX wherein $R_2$ is as above.

The conversion of the lactam of formula V to the compound of formula IX, via the intermediates of formulae VII and VIII, can be carried out in a conventional manner by treating the lactam of formula V with a lower alkyl or phenyl chloroformate, preferably a lower alkyl chloroformate, in the presence of a nitrogen-containing base. In carrying out this reaction, any conventional nitrogen-containing base, such as the primary, secondary, and tertiary amines, set forth above, can be utilized. This reaction can be suitably carried out in an inert organic solvent. In this reaction, any conventional inert organic solvent can be utilized, with the dilower alkyl ketones, particularly acetone, being preferred. In carrying out this reaction, temperature and pressure are not critical, and this reaction can be suitably carried out at from about 0° C. to about 30° C. and at atmospheric pressure. Preferably, this reaction is carried out at about room temperature.

The imido-anhydride of formula IX is then converted to an azido-carbonyl compound of the formula:

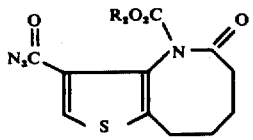

X wherein $R_2$ is as above.

The imido-anhydride of formula IX can be converted to the azidocarbonyl compound of formula X by treating the compound of formula IX in a conventional manner with an alkali metal azide. This reaction, can be carried out in an inert organic solvent. In this reaction, any conventional inert organic solvent, such as the dilower alkyl ketones, can be utilized. In this reaction, temperature and pressure are not critical, and the reaction can be suitably carried out at from about −10° C. to about +30° C. and at atmospheric pressure. Preferably, this reaction is carried out at about 0° C.

The azidocarbonyl compound of formula X is then converted to an isocyanate of the formula:

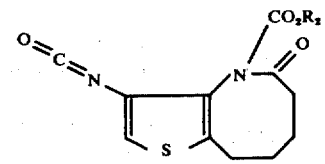

XI wherein $R_2$ is as above;
which, in turn, is converted to a urethane of the formula:

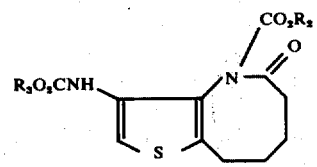

XII wherein $R_2$ is as above; and $R_3$ is aliphatic hydrocarbyl, cycloaliphatic hydrocarbyl or aryl lower alkyl;
and which, in turn, is converted to diurethane of the formula:

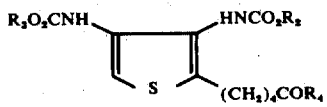

XIII wherein $R_2$ and $R_3$ are as above; and $R_4$ is hydroxy, lower alkoxy, aryl lower alkoxy, amino, monoloweralkylamino, diloweralkylamino, arylamino or arylloweralkylamino.

The azidocarbonyl compound of formula X can be converted to the isocyanate of formula XI and the urethane of formula XII by heating the azidocarbonyl compound of formula X in the presence of an alcohol. In this reaction, any primary, secondary, or tertiary alcohol can be utilized. Among the alcohols which can be utilized are the aliphatic hydrocarbyl alcohols, such as ethanol, methanol, allyl alcohol, propargyl alcohol, hexenyl alcohol and decanyl alcohol, the cycloaliphatic hydrocarbyl alcohols, such as menthol, borneol and cholesterol, and the aryl lower alkanols, such as benzyl alcohol. This reaction can be suitably carried out in an inert organic solvent. In this reaction, any conventional inert organic solvent can be utilized, as for example, hexane, chloroform and benzene. Preferably, this reaction is carried out in an excess of the alcohol, which serves as the solvent medium. In carrying out this reaction, temperature and pressure are not critical, and temperatures of from about 50° C. to the reflux temperature of the alcoholic mixture and atmospheric pressure can be conveniently utilized. Preferably, this reaction is carried out at from about 70° C. to 75° C.

In carrying out the thermolysis of the azidocarbonyl compound of formula X to form the isocyanate of formula XI, which is in turn converted by the alcohol to the urethane of formula XII, it is preferred to treat the azidocarbonyl compound of formula X with a lower alkanol or an aryl lower alkanol. By so doing, a diurethane compound of formula XIII is obtained wherein $R_3$ is lower alkyl or aryl lower alkyl and $R_4$ is lower alkoxy or aryl lower alkoxy.

However, where the azidocarbonyl compound of formula X is treated with an alcohol other than a lower alkanol or aryl lower alkanol, it is preferred to treat this compound with an optically active alcohol. In this reation step, any conventional, optically active alcohol can be utilized, such as d- or l-borneol, isopinocampheol or menthol.

Where the azidocarbonyl compound of formula X is treated with an alcohol other than a lower alkanol or aryl lower alkanol, the urethane of formula XII which results is not converted further by the alcohol utilized to the corresponding diurethane compound of formula XIII. In such a case, it is necessary to convert the urethane of formula XII to the diurethane compound of formula XIII in a separate step. The conversion of the urethane of formula XII to the diurethane compound of formula XIII, wherein $R_4$ is hydroxy, can be carried out by any conventional method of hydrolyzing an imide. Preferably, the urethane of formula XII is hydrolyzed by treating it with an alkali metal hydroxide or an alkaline earth metal hydroxide, to convert it to the diurethane compound of formula XIII. Alternatively, the urethane of formula XII can be treated with ammonia, a mono- or di-loweralkylamine, such as methylamine or diethylamine, an arylamine, such as phenylamine, or an arylloweralkylamine, such as benzylamine, to convert it to the diurethane compound of formula XIII, wherein $R_4$ is amino, monoloweralkylamino, diloweralkylamino, arylamino or arylloweralkylamino. In carrying out these reactions for obtaining the diurethane of formula XIII, temperature and pressure are not critical, and temperatures from about 50° C. to 100° C. and atmospheric pressure can be suitably utilized. These reactions are also suitably carried out in a conventional, inert organic solvent, such as a lower alkanol, particularly methanol.

The diurethane compound of formula XIII, wherein $R_4$ is other than hydroxy, whether formed by the preferred, one step treatment of the azidocarbonyl compound of formula X with a lower alkanol or aryl lower alkanol or formed by treating the urethane of formula XII with ammonia or an amine, is then hydrolyzed with a base. This basic hydrolysis can be carried out in a conventional manner, such as by the procedure set forth above for hydrolyzing the amine of formula III. The resulting thiophenevaleric acid has the structural formula:

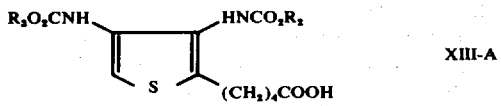

XIII-A wherein $R_2$ and $R_3$ are as above;
and is the same valeric acid compound obtained by first treating the azido-carbonyl compound of formula X with an alcohol, other than a lower alkanol or aryl lower alkanol, and then hydrolyzing the resulting urethane compound of formula XII.

The thiophenevaleric acid of formula XIII-A is then converted to a tetrahydrothiophenevaleric acid of the formula:

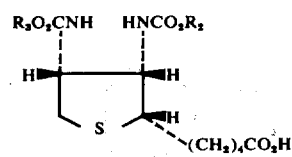

XIV.

wherein $R_2$ and $R_3$ are as above.

The tetrahydrothiophenevaleric acid formula XIV is obtained by the catalytic hydrogenation of the thiophenevaleric acid formula XIII-A in the presence of an acid. In carrying out this reaction, any conventional, noble metal hydrogenation catalyst, such as platinum, palladium, ruthenium or rhodium, can be utilized. The preferred hydrogenation catalyst is a palladium catalyst. This reaction is suitably carried out in an inert organic solvent. In this reaction, any conventional inert organic solvent in which the thiophenevaleric acid compound of formula XIII-A and catalytic quantities of an acid are soluble is suitable. Among the preferred, inert organic solvents are the lower alkanols, such as methanol and ethanol, and the cyclic ethers, such as dioxane and tetrahydrofuran. Especially preferred inert organic solvents for carrying out this reaction are the lower alkanoic acids, particularly glacial acetic acid, in which the addition of catalytic amounts of an acid to the solvent may be dispensed with. In carrying out this reaction in an inert organic solvent, other than an alkanoic acid, any conventional carboxylic acid may be utilized to catalyze the hydrogenation. The preferred acids for this purpose are the lower alkanoic acids, such as formic, acetic and pentanoic acid, the lower alkane dicarboxylic acids, such as succinic acid, and the aryl lower-alkanoic acids, such as benzoic acid. In carrying out this reaction, temperature and pressure are not critical, and temperatures from about 25° C. to about 110° C. and pressures of from about 1,000 to about 3,000 p.s.i. can be conveniently utilized. Preferably, temperatures of about 50° C. to 100° C., particularly about 75° C., and pressures of about 1500 to 2000 p.s.i., particularly about 1800 p.s.i., are utilized.

In the hydrogenation of the thiophenevaleric acid of formula XIII-A in accordance with this application, it has been found that the resulting tetrahydrothiophenevaleric acid of formula XIV is typically obtained as a racemate. However, it has been surprisingly found that the hydrogenation, as set forth above, of the compound of formula XIII-A, wherein $R_3$ is a residue of an optically active alcohol, formed, for example, by heating the azidocarbonyl compound of formula X with an optically active alcohol, yields a mixture of enantiomers of the tetrahydrothiophenevaleric acid of formula XIV in which one of the enantiomers predominates. Whether a particular $R_3$ enantiomer residue on the compound of formula XIII-A will yield a tetrahydrothiophenevaleric acid of formula XIV enriched in the d- or the l-enantiomer cannot be predicted without actually carrying out a hydrogenation with the particular, optically active residue. However, when it is determined that hydrogenation of a particular compound of formula XIII-A, which includes a particular $R_3$-enantiomer residue (e.g., a d-enantiomer residue), yields predominately one enantiomer (e.g., an l-enantiomer) of the compound of formula XIV, then it can be predicted that hydrogenation of the same compound of formula XIII-A, which includes the other $R_3$ enantiomer residue (i.e., the l-enantiomer residue), will yield predominately the other enantiomer (i.e., the d-enantiomer) of the compound of formula XIV.

The tetrahydrothiphenevaleric acid of formula XIV, whether a racemate, an enantiomer, or a mixture of enantiomers, is then converted to biotin by the basic hydrolysis of the compound of formula XIV. The resulting biotin will have an optical activity corresponding to the optical activity of the tetrahydrothiophenevaleric acid of formula XIV from which it was made. This hydrolysis can be carried out in a conventional manner, such as by the procedure set forth above for hydrolyzing the amine of formula III. Preferably, the tetrahydrothiophenevaleric acid of formula XIV is hydrolyzed by heating it in an aqueous solution containing an alkali metal hydroxide or an alkaline earth metal hydroxide. In carrying out this reaction, temperature and pressure are not critical, and the reaction can be suitably carried out at from about 50° C. to about 100° C. and at atmospheric pressure. Preferably, the aqueous solution containing the base and the tetrahydrothiphenevaleric acid of formula XIV is heated to reflux.

Also, in accordance with this invention, d,1-biotin is obtained from the 4,5-dihydrothiophene of formula I by first converting the lactam of formula VI to a hydrazide compound of the formula:

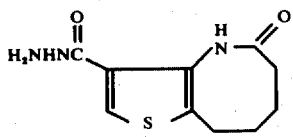

XV.

The lactam of formula VI can be converted to the hydrazide of formula XV by any conventional method of hydrazinolizing an ester. Preferably, this reaction is carried out by treating the lactam of formula VI with hydrazine. This reaction can be carried out in an inert solvent, such as water or a lower alkanol. Preferably, this reaction is carried out in an excess of hydrazine, utilizing no inert solvent medium. In carrying out this reaction, temperature and pressure are not critical, and the reaction can be suitably carried out at room temperature and atmospheric pressure.

The hydrazide compound of formula XV is then converted to an azidocarbonyl compound of the formula:

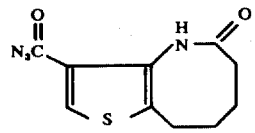

XVI.

The hydrazide of formula XV can be converted to the azidocarbonyl compound of formula XVI by a conventional, nitrous acid oxidation of carbohydrazide to an acylazide. Preferably, this reaction is carried out by treating the hydrazide of formula XV with an alkali metal nitrite in an aqueous mineral acid, especially a hydrohalic acid, particularly hydrochloric acid. In carrying out this reaction, temperature and pressure are not critical, and this reaction can be suitably carried out at from about −20° C. to about +10° C. and at atmospheric pressure. Preferably, this reaction is carried out at about 0° C.

The azidocarbonyl compound of formula XVI is then converted to an isocyanate of the formula:

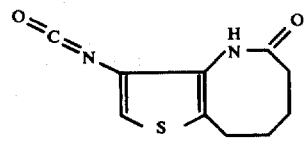

XVII which is, in turn, converted to a urethane of the formula:

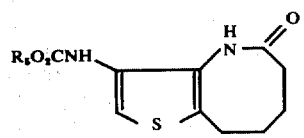

XVIII wherein $R_5$ is aliphatic hydrocarbyl, cycloaliphatic hydrocarbyl or aryl lower alkyl.

The azidocarbonyl compound of formula XVI can be converted to the isocyanate of formula XVII, which is, in turn, converted to the urethane of formula XVIII, by heating the azidocarbonyl compound of formula XVI in the presence of an alcohol. This reaction can be carried out in a conventional manner, such as by the procedure set forth above for converting the azidocarbonyl compound of formula X to the urethane of formula XII. In carrying out this procedure, it is preferred to react the azidocarbonyl compound of formula XVI with an aliphatic hydrocarbyl alcohol, a cycloaliphatic hydrocarbyl alcohol or an aryl lower alkyl alcohol. Especially preferred alcohols are the lower alkyl alcohols and benzyl alcohol.

The urethane of formula XVIII can also be obtained by first converting the lactam of formula V to an amide of the formula:

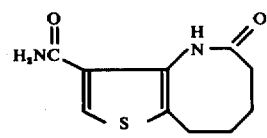

V-A and treating and amide of formula V-A with chlorine or bromine in the presence of an alkali metal or alkaline earth metal alkoxide or hydroxide and in the presence of an alcohol, such as an aliphatic hydrocarbyl alcohol, cycloaliphatic hydrocarbyl alcohol or aryl lower alkyl alcohol.

The lactam of formula V can be converted to the amide of formula V-A by any conventional method of converting a carboxylic acid to a carboxamide. Preferably the lactam of formula V is treated first with a chlorinating or brominating agent, such as thionyl chloride or thionyl bromide, to form the corresponding acyl halide. This reaction can be suitably carried out in an inert organic solvent. In this reaction, any conventional, inert organic solvent, as for example chloroform or benzene, can be utilized. In carrying out this reaction, temperature and pressure are not critical, and this reaction can be suitably carried out at from about 25° C. to about 75° C. and at atmospheric pressure. The resulting acyl halide is, then, preferably treated with ammonia. This reaction can be suitably carried out in an inert organic solvent. In this reaction, any conventional inert organic solvent, as for example benzene or chloroform, can be utilized. In this reaction, temperature and pressure are not critical, and temperatures of about −15° C. to +50° C. and atmospheric pressure can be suitably utilized.

The amide of formula V-A is then converted to the urethane of formula XVIII by treating it with chlorine or bromine in the presence of an alkali metal or alkaline earth metal hydroxide or alkoxide and an alcohol. This reaction can be suitably carried out in a conventional manner in an inert organic solvent. In this reaction, any conventional, inert organic solvent, as for example chloroform or benzene, can be utilized. Preferably, this reaction is carried out in an excess of the alcohol, which serves as the solvent medium. In carrying out this reaction, temperature and pressure are not critical, and this reaction can be suitably carried out at 25° C. to 120° C. and atmospheric pressure.

The urethane of formula XVIII is then converted to a tetrahydrothiophene of the formula:

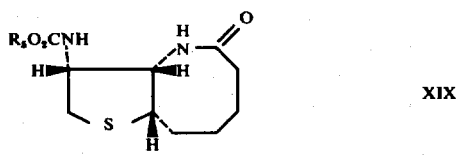

wherein $R_5$ is as above.

The urethane of formula XVIII is converted to the tetrahydrothiophene of formula XIX by the hydrogenation in the presence of a noble metal catalyst. In carrying out this hydrogenation, the urethane is preferably hydrogenated utilizing the procedure set forth above for hydrogenating the thiophenevaleric acid of formula XIII-A.

The tetrahydrothiophene of formula XIX is then converted to a bis-amino acid of the formula:

The tetrahydrothiophene of formula XIX can be converted to the bis-amino acid of formula XX by any conventional basic hydrolysis whereby a lactam is converted to an amino acid. In carrying out this basic hydrolysis, it it preferred to utilize the procedure, set forth above, for hydrolyzing an amine of formula III.

The bis-amino compound of formula XX is then converted to d,1-biotin by treating the bis-amino compound with phosgene. The bis-amino compound of formula XX can be treated in a conventional manner with phosgene to form d,1-biotin. Preferably, this reaction is carried out by dissolving the bis-amino compound in an aqueous base, preferably sodium carbonate, and then introducing phosgene into the solution. In this reaction, temperature and pressure are not critical, and temperatures of from about −20° C. to +25° C. and atmospheric pressure can be suitably utilized. Preferably, this reaction is carried out at about 0° C.

The biotin which is obtained by the process of this application can be obtained in pure form as the free acid, or, if desired, can be esterified in a conventional manner with a lower alkanol to form the corresponding ester.

The 4,5-dihydrothiophene compounds of formula I, which are the starting materials for the process described in this application, are generally known. In Baker et al., *J. Org. Chem.*, 12, 167 (1947), the preparation of 4-carbomethoxy-2-(4,5-dihydrothiophen-3(2H)-one)valeric acid methyl ester is described. Utilizing conventional hydrolysis and trans-esterification procedures, this dihydrothiophene compound can be conveniently converted to form the other 4,5-dihydrothiophene compounds of formula I of this application.

The examples which follow further illustrate this invention. All temperatures are in degrees Centigrade.

EXAMPLE 1

A solution of 151.4 g. (.553 mole) of 4-carbomethoxy-2-(4,5-dihydrothiophen-3(2H)-one)valeric acid methyl ester in 470 ml. of pyridine was treated with 42.2 g. (0.608 mole) of hydroxylamine hydrochloride, and the reaction mixture was stirred at 25° C. for 24 hours. Excess pyridine was removed on the rotary evaporator. The residue was taken up in 500 ml. of dichloromethane and washed with 200 ml. of 1N hydrochloric acid. The organic layer was dried over anhydrous sodium sulfate and evaporated to dryness to yield 158.0 g. (.546 mole, 99%) of 4-carbomethoxy-2-(4,5-dihydrothiophen-3(2H)-one)valeric acid methyl ester oxime as a pale yellow oil.

EXAMPLE 2

Into a solution of 110 g. (.381 mole) of 4-carbomethoxy-2-(4,5-dihydrothiophen-3(2H)-one)valeric acid methyl ester oxime in 1500 ml. anhydrous diethyl ether, submerged in an ice bath, was bubbled hydrogen chloride gas. After ¼ hr., the flask containing the reaction mixture was stoppered and the reaction allowed to proceed at 25° C. for 24 hrs. The reaction mixture was concentrated on a rotary evaporator, and the residue was taken up in 500 ml. water and made basic by the addition of 1000 ml. 10% by weight aqueous sodium bicarbonate solution. The reaction mixture was then extracted three times with 500 ml. portions of dichloromethane. The organic phases were dried over anhydrous sodium sulfate and evaporated to afford 90.0 g. (.316 mole, 83%) of 3-amino-4-carbomethoxy-2-thiophenevaleric acid methyl ester as a pale yellow crystalline solid; m.p. 50°–52°. The aqueous phase was acidified with 6N hydrochloric acid to pH 4 and extracted three times with 300 ml. portions of dichloromethane. The organic phase was dried over anhydrous sodium sulfate and evaporated to afford 13.0 g. (.048 mole, 13%) of 3-amino-4-carbomethoxy-2-thiophenevaleric acid as a white solid m.p. 130°–132°. An analytical sample was obtained by recrystallization from ethyl acetate; m.p. 131°–132°.

EXAMPLE 3

A solution of 18.64 g. (0.0687 mole) of 3-amino-4-carbomethoxy-2-thiophenevaleric acid methyl ester in 400 ml. of methanol was treated with 185 ml. (0.185 mole) of 1N sodium hydroxide. The reaction mixture was refluxed for one hour, cooled, and concentrated. The residue, consisting essentially of 3-amino-4-carbomethoxy-2-thiophenevaleric acid, was acidified to pH 1 with 50 ml. 6N hydrochloric acid and evaporated to dryness leaving 16.64 g. (0.0685 mole, 100%) of 3-amino-4-carboxy-2-thiophenevaleric acid as a white solid, admixed with 7.0 g. of the sodium chloride by-product. Purification was achieved by extraction with hot ethanol. The product was recrystallized from methanol/diethyl ether.

EXAMPLE 4

A suspension of 0.45 g. (0.00185 mole) of 3-amino-4-carboxy-2-thiophenevaleric acid in 40 ml. of xylene was heated to reflux and maintained at that point, employing a Dean-Stark trap to remove water. After 1 day, the system was homogeneous. The xylene was decanted from the polymeric by-product, which adhered to the reaction flask, and the flask was then washed with 15 ml. of hot xylene. The xylene portions were combined and evaporated under vacuum. The residue was partitioned between 30 ml. of dichloromethane and 60 ml. of 10% by weight aqueous sodium bicarbonate solution. The aqueous phase was acidified to pH 1 with 6N hydrochloric acid and extracted three times with 30 ml. portions of dichloromethane. The organic phases were combined, dried, and evaporated to yield 0.361 g. (0.00160 mole, 87% of 3-amino-4-carboxy-2-thiophenevaleric acid-zeta-lactam as an off-white solid. After a recrystallization from xylene-ethanol/pet. ether, the product had a m.p. 215°–217° C.

EXAMPLE 5

A suspension of 15.0 g. (0.0554 mole) of 3-amino-4-carbomethoxy-2-thiophenevaleric acid in 1500 ml. of xylene was heated to reflux and maintained at that temperature for 1 week employing a Dean-Stark trap to remove water. The solvent was removed on the rotary evaporator using a high vacuum pump. The residue was taken up in 100 ml. dichloromethane and washed with 30 ml. of 10% by weight aqueous sodium bicarbonate solution. The organic layer was dried over anhydrous sodium sulfate and evaporated to afford 13.5 g. (0.0534 mole, 96%) of crude 3-amino-4-carbomethoxy-2-thiophenevaleric acid lactam. Recrystallization from ethyl acetate yielded 11.8 g. (0.0467 mole, 84%) of the product as a white solid; m.p. 167°–168° C.

EXAMPLE 6

To a solution of 4.8 g. (0.020 mole) of 3-amino-4-carbomethoxy-2-thiophenevaleric acid lactam in 60 ml. of methanol was added 28 ml. (0.022mole) of 1N sodium hydroxide. The solution was refluxed for 20 minutes, cooled, and concentrated. The basic residue was extracted twice with 75 ml. portions of methylene chloride, after the addition of 50 ml. of water. The aqueous phase was acidified to pH 1 by the addition of 25 ml. of 1N hydrochloric acid and extracted three times with 75 ml. portions of dichloromethane. These dichloromethane extracts were dried over sodium sulfate, and evaporated to afford 4.3 g. (0.019 mole, 96%) of 3-amino-4-carboxy-2-thiophenevaleric acid-zeta-lactam as a white solid. The analytical sample, m.p. 216°–217° C., was prepared by recrystallization from xylene-ethanol/pet. ether.

EXAMPLE 7

2.25 g. (0.010 mole) of 3-amino-4-carboxy-2-thiophenevaleric acid-zeta-lactam was dissolved in 40 ml. of acetone to which 2 ml. of water had been added, and the solution was cooled in an ice-bath for 15 minutes. At this point, 4.6 ml. (0.033 mole) of triethylamine in 40 ml. of acetone was added, followed immediately by the dropwise addition of 3.3 ml. (0.033 mole) of ethyl chloroformate in 4.5 ml. of acetone over a 10 minute period. The reaction mixture was stirred at 0° C. for 1 hour to form 3-amino-4-carbethoxyoxycarbonyl-2-thiophenevaleric acid lactam, which in turn was converted to 3-carbethoxyamino-4-carboxy-2-thiophenevaleric acid lactam, which in turn was converted to 3-carbethoxyamino-4-carbethoxyoxycarbonyl-2-thiophenevaleric acid lactam.

A solution of 2.13 g. (0.033 mole) sodium azide in 10 ml. of water was then added dropwise over a 5-minute period to the reaction mixture. The reaction was further stirred at 0° C. for 2 hours. The reaction mixture was then partitioned between 100 ml. of dichloromethane and 75 ml. of ice water. The aqueous phase was then extracted three times with 30 ml. portions of dichloromethane. The organic extracts were dried over anhydrous sodium sulfate, filtered, and evaporated to leave 3.20 g. (0.009 mole, 100%) of 4-azidocarbonyl-3-carbethoxyamino-2-thiophenevaleric acid lactam as a crystalline solid.

EXAMPLE 8

3.20 g. (0.099 mole) of 4-azidocarbonyl-3-carbethoxyamino-2-thiophenevaleric acid lactam was dissolved in 75 ml. of methanol, and the temperature was raised slowly to reflux over 15 minutes. The reaction was allowed to proceed for 6 hours at this temperature. Formed as intermediate in the reaction mixture was 3-carbethoxyamino-4-isocyanato-2-thiophenevaleric acid lactam, which was in turn converted to 3-carbethoxyamino-4-carbomethoxyamino-2-thiophenevaleric acid lactam. The methanol was then removed, leaving 3.12 g. (0.087 mole, 87%) of 3-carbethoxyamino-4-carbomethoxyamino-2-thiophenevaleric acid methyl ester as an oil; recrystallization from diethyl ether yielded a white solid; m.p. 60°–61° C.

EXAMPLE 9

0.136 g. (0.000380 mole) of 3-carbethoxyamino-4-carbomethoxyamino-2-thiophenevaleric acid methyl ester was dissolved in 5 ml. of methanol and treated with 0.55 ml. of 1N sodium hydroxide. The reaction mixture was refluxed for 3 hours, and then cooled, and the methanol was then evaporated. The residue was taken up in 30 ml. of dichloromethane and treated with 30 ml. of water. After separating the process, the aqueous phase was acidified with 2 ml. of 1N hydrochloric acid and extracted three times with 30 ml. portions of dichloromethane. The organic phases were cooled, dried over anhydrous sodium sulfate, and evaporated to yield 0.129 g. (0.000376 mole, 99%) of 3-carbethoxyamino-4-carbomethoxyamino-2-thiophenevaleric acid as a white solid. An analytical sample was prepared by recrystallization from methanol; m.p. 159°–160° C.

EXAMPLE 10

0.344 g. (0.001 mole) of 3-carbethoxyamino-4-carbomethoxyamino-2-thiophenevaleric acid was dissolved in 200 ml. of glacial acetic acid and subjected to 1800 psi. hydrogen gas in a steel autoclave at 50° C. for 10 hrs., in the presence of 2.0 g. of 10% Pd/C catalyst. After cooling to room temperature (22° C.), the autoclave was vented, and the catalyst was filtered and washed with 100 ml. of glacial acetic acid. The solvent was removed under vacuum to afford 0.328 g. (0.00095 mole, 95%) of all cis d,1-3-carbethoxyamino-4-carbomethoxyamino-2-tetrahydrothiophenevaleric acid as a colorless oil.

EXAMPLE 11

0.208 g. (0.0006 mole) of all cis d,1-3-carbethoxyamino-4-carbomethoxyamino-2-tetrahydrothiophenevaleric acid was dissolved in 1.8 ml. (0.0018 mole) of 1N sodium hydroxide. The reaction solution was refluxed for 4.0 hrs. At this point, the pH was adjusted to 1 by the addition of 3 ml. of 1N hydrochloric acid. The solvent was removed to leave a tan crystalline residue. Upon addition of 5 ml. of water, a solid remained out of solution, which was filtered and dried to yield 0.050 g. (0.00021 mole, 35%) of d,1-biotin, which could be recrystallized from water; m.p. 232°–233° C.

EXAMPLE 12

15.0 g. (0.0628 mole) of 3-amino-4-carbomethoxy-2-thiophenevaleric acid lactam was dissolved at 25° C. in 25 ml. of 95% hydrazine. After 10 minutes, the product began to crystallize. The reaction was allowed to proceed for ½ hr., and then, the reaction mixture was concentrated. The residue was filtered and washed with cold ethanol to afford 15.0 g. (0.0628 mole, 100%) of 3-amino-4-carbazoyl-2-thiophenevaleric acid lactam; m.p. 191°–192° C.

An analytical sample was prepared by recrystallization from ethanol.

EXAMPLE 13

To a solution of 12.24 g. (0.052 mole) of 3-amino-4-carbazoyl-2-thiophenevaleric acid lactam in 200 ml. of 1N hydrochloric acid was added dropwise at 0° C. 4.4 g. (0.062 mole) of sodium nitrite in 30 ml. of water (previously cooled to 0°) over a 14-minute period. The heterogeneous mixture was stirred for ½ hr., and the mixture was further extracted five times with 50 ml. portions of chloroform. The extracts were dried over anhydrous sodium sulfate and evaporated to afford 13.0 g. (0.052 mole, 100%) of 3-amino-4-azidocarbonyl-2-thiophenevaleric acid lactam as a colorless oil.

EXAMPLE 14

13.0 g. (0.052 mole) of 3-amino-4-azidocarbonyl-2-thiophenevaleric acid lactam was dissolved in 500 ml. of dry methanol, and the temperature was raised to 50° C. After 15 min. at that temperature, the solution was carefully brought up to reflux. The rate of heating was determined by the amount of vigorous gas evolution. The solution was refluxed for 6.0 hrs. Formed as an intermediate in the reaction mixture was 3-amino-4-isocyanato-2-thiophenevaleric acid lactam. The solution was then cooled and evaporated to afford 12.5 g. (0.0491 mole, 95%) of 3-amino-4-carbomethoxyamino-2-thiophenevaleric acid lactam as a white crystalline solid; m.p. 208°–210° C.

EXAMPLE 15

1.0 g. (0.004 mole) of 3-amino-4-carbomethoxyamino-2-thiophenevaleric acid lactam was dissolved in 200 ml. of glacial acetic acid and placed in a steel autoclave. After addition of 2.0 g. of 10% Pd/C catalyst the reaction mixture was hydrogenated at 100° C. and 1800 psi for 10.0 hrs. The autoclave was cooled, vented, and the catalyst was filtered and washed with 100 ml. of acetic acid. The solvent was removed, and the cis d,1-3-amino-4-carbomethoxyamino-2-tetrahydrothiophenevaleric acid lactam residue was taken up in 50 ml. of water to which 10.0 g. Ba(OH)$_2$·8H$_2$O had been added.

The reaction mixture was refluxed for 20.0 hours and cooled. Carbon dioxide was bubbled in until the pH dropped to 4. The precipitated barium carbonate was filtered and washed with 20 ml. of water. The filtrate was acidified with 1N sulfuric acid until acid turned to congo red. The precipitated barium sulfate was filtered. The filtrate was evaporated to dryness, and the residue was taken up in 120 ml. of 10% by weight sodium carbonate and cooled to 0° C. Gaseous phosgene was then bubbled in for 25 minutes until the medium was acidic to congo red. After 2.0 hrs., an impurity was filtered, and the filtrate was evaporated to dryness. The d,1-biotin residue was suspended in 70 ml. of dry methanol and treated with 1 drop of sulfuric acid. The mixture was refluxed to 1 hour, cooled, and filtered. The salt was washed three times with 10 ml. portions of methanol. The filtrate was evaporated, and the residue was partitioned between 50 ml. of chloroform and 20 ml. of water. The aqueous phase was extracted three times with 20 ml. portions of chloroform. The organic phases were combined, dried over anhydrous sodium sulfate, and evaporated to give 0.300 g. (.00116 mole, 29%) of crude d,1-biotin methyl ester. The mixture was taken up in 3 ml. of dichloromethane and plated on three, thick layer silica plates. Elution was with 10% by volume methanol/chloroform solution. After two elutions 0.042 g. (0.000163 mole, 4%) of pure d,1-biotin methyl ester, m.p. 131°–132° C., was obtained by removal of the band at $R_f$=0.26.

EXAMPLE 16

A suspension of 2.25 g. (0.010 mole) of 3-amino-4-carboxy-2-thiophenevaleric acid-zeta-lactam in 200 ml. of chloroform was treated with 10 ml. of thionyl chloride. The reaction was refluxed for 2.0 hrs., cooled and evaporated to afford 3-amino-4-chlorocarbonyl-2-thiophenevaleric acid lactam as a yellow solid. The yield was quantitative after drying under high vacuum.

EXAMPLE 17

Ammonia was bubbled into a solution of 2.60 g (0.010 mole) of 3-amino-4-chlorocarbonyl-2-thiophenevaleric acid lactam in 200 ml of benzene at 0° C. for 20 minutes. The solution was then stirred at 25° C. for 2.0 hrs. and evaporated. The solid residue was suspended in water and filtered to afford pure 3-amino-4-carboxamido-2-thiophenevaleric lactam as a cream-colored solid quantitatively yield.

EXAMPLE 18

3.56 g (0.010 mole) of 4-azidocarbonyl-3-carbethoxyamino-2-thiophenevaleric acid lactam was dissolved in 100 ml benzene. To this solution was added 3.08 g (0.020 mole) of (+)-isopinocampheol, and the reaction was brought to reflux and maintained at that temperature for 16 hrs. After cooling, the reaction was concentrated to afford 7.0 g of a residue, containing 4-pinyloxyamino-3-carbethoxyamino-2-thiophenevaleric acid lactam which was up in 175 ml of methanol. The solution was treated with 50 ml of 1N sodium hydroxide and subsequently refluxed 0.5 hr. After cooling to 25° C., a solid impurity was filtered off, and the filtrate was concentrated. The residue was partitioned between 30 ml of diethyl ether and 50 ml of 1N sodium hydroxide. The ether phase was concentrated to afford 1.8 g of recovered alcohol. The aqueous phase was acifified to pH 1 with 1N HCl and extracted three times with 30 ml portions of dichloromethane. The organic extracts were dried over sodium sulfate and evaporated to yield 3.55 g (0.0076 mole, 76 %) of 3-carbethoxyamino-4-carbo-3-pinyloxyamino-2-thiophenevaleric acid as a viscous oil.

EXAMPLE 19

0.466 g (0.001 mole) 3-carbethoxyamino-4-carbo-3-pinyloxyamino-2-thiophenevaleric acid was hydrogenated in 200 ml of acetic acid at 50° C/1800 psi over a 10 hr. period. The catalyst loading was 2.0 g. The autoclave was cooled overnight, and the catalyst was filtered. The filtrate was evaporated to dryness to afford 0.460 g (0.001 mole, 100%) of all-cis-3-carbethoxyamino-4-carbo-3-pinyloxyamino-2-tetrahydrothiophenevaleric acid as a colorless oil.

EXAMPLE 20

0.455 g (0.96 mmole) of the all-cis-3-carbethoxy-4carbo-3-pinyloxyamino-2-tetrahydrothiophenevaleric acid, prepared in Example 18, was dissolved in 3.5 ml of 1N sodium hydroxide. After dilution with 3 ml. of water, the reaction was refluxed for 5.0 hrs., cooled, and partitioned between 20 ml ethylacetate and 10 ml water. After three 10 ml extractions with ethyl acetate, the aqueous phase was acififed with 1N HCl to pH 1 and concentrated. Upon cooling, the concentrate deposited 0.080 g (0.328 mole, 34%) of biotin. The compound was collected by filtration and recrystallized from water. $[\alpha]_D^{25} = +4°$, corresponding to an optical induction of 4.5% with an enantiomeric excess of d-biotin.

EXAMPLE 21

3.56 g (0.010 mole) of 4-azidocarbonyl-3-carbethoxyamino-2-thiophenevaleric acid lactam was dissolved in 100 ml of benzene. To this solution was added 3.08 g (0.020 mole) of l-borenol, and the reaction was then refluxed overnight, cooled, concentrated, and taken up in 250 ml of methanol. The solution containing 3-carbethoxyamino-4-carbo-2-1-bornyloxyamino-2-thiophenevaleric acid lactam, was treated with 50 ml of 1N sodium hydroxide and refluxed 0.45 hr. The reaction was cooled and concentrated, and the residue was partitioned between 30 ml of diethyl ether and 50 ml of 1N sodium hydroxide. The ether phase was discarded and the aqueous phase was acidified to pH 1 with 1N HCl. The mixture was extracted three times with 20 ml portions of dichloromethane. The organic extracts were dried over sodium sulfate and evaporated by yield 2.76 g (0.0059 mole, 59%) of 3-carbethoxyamino-4-carbo-2-1-bornyloxy-amino-2-thiophenevaleric acid as a colorless foam.

EXAMPLE 22

0.466 g (.001 mole) of 3-carbethoxyamino-4-carbo-2-1-bornyloxyamino-2-thiophenevaleric acid was hydrogenated in 200 ml of acetic acid at 50° C/1800 psi over a 10 hr. period. The catalyst loading was 2.0 g. The autoclave was cooled overnight, and the catalyst was filtered. The filtrate was evaporated to dryness to yield 0.0470 g (100%) of all-cis-4-carbo-2-bornyloxyamino-3-carbethoxyamino-2-tetrahydrothiopheneval-eric acid as a colorless oil.

EXAMPLE 23

0.0470 g (0.001 mole) of the all cis-4-carbo-2-1-bornyloxyamino-3-carbethoxyamino-2-tetrahydrothiophenevaleric acid prepared in Example 22, was dissolved in 4 ml of 1N sodium hydroxide. After dilution with 5 ml of water, the reaction was allowed to reflux overnight. The reaction mixture was cooled, extracted with ethyl acetate, and the aqueous phase was acidified to pH 1 with 1N HCl. After a further extraction with ethyl acetate, the aqueous phase was evaporated to dryness. The residue was dissolved in 25 ml of 10% by wt. potassium carbonate, and phosgene was bubbled in until the pH was acid to congo red. The mixture was again evaporated to dryness. The residue was suspended in 50 ml of methanol and two drops of conc. sulfuric acid were added. After a reflux period of 1 hour, the reaction was cooled and evaporated. The residue was partitioned between 30 ml of methylene chloride and 20 ml of water. The aqueous layer was further extracted three times with 25 ml portions of methylene chloride. The organic phases were combined, dried over sodium sulfate, and evaporated to yield .085 g of crude d,1-biotin methyl ester. Purification was achieved by chromatography on silica; the solvent system was benzene/ethyl acetate/acetic acid (60:35:5 parts by volume). From the chromatogram, 0.040 g (0.085 mmole, 8.5%) of crystalline biotin methyl ester was isolated. $[\alpha]_D^{25} = -5°$ ($c = 0.40$, $CH_3OH$), corresponding to an optical induction of 7% with an enantiomeric excess of l-biotin.

EXAMPLE 24

0.0356 g (0.001 mole) of 4-aziodcarbonyl-3-carbethoxyamino-2-thiophenevaleric acid lactam was dissolved in 20 ml of benzene. After the addition of 0.344 g (0.0022 mole) of 1-menthol, the reaction mixture was refluxed 1.5 hrs., cooled, and evaporated. The 3-carbethoxyamino-4-carbo-p-menth-3-yloxyamino-2-thiophenevaleric acid lactam residue was taken up in 20 ml of methanol and treated with 5 ml of 1N sodium hydroxide. After a reflux period of 2.5 hrs., the reaction was cooled, concentrated, and the residue was partitioned between 20 ml of diethyl ether and 40 ml of 1N sodium hydroxide. The ether phase, containing excess 1-menthol, was discarded, and the aqueous layer was acidified to pH 1 with 1N HCl. The mixture was then extracted three times with 20 ml portions of dichloromethane. The organic extracts were dried over sodium sulfate and evaporated to afford a residue, which was chromatographed on thick layer silica plates (solvent system: 5% by volume $CH_3OH/CHCl_3$). From the chromatogram, 0.400 g (0.0086 mole, 86%) of 3-carbethoxyamino-4-carbo-p-menth-3-yloxy-amino-2-thiophenevaleric acid was isolated as a colorless viscous oil.

EXAMPLE 25

0.200 g (0.427 mmole) of 3-carbethoxyamino-4-carbo-p-menth-3-yloxyamino-2-thiophenevaleric acid 1 was hydrogenated in 200 ml of acetic acid at 50° C/1800 psi over a 10 hr. period. The catalyst loading was 2.0 g 10% Pd/C. The autoclave was cooled overnight, and the catalyst was filtered. The filtrate was evaporated to dryness to leave 0.200 g (0.427 mmole, 100%) of all cis-3-carbethoxyamino-4-carbo-p-menth-3-yloxyamino-2-tetrahydrothiophenevaleric acid 2, as a colorless oil.

EXAMPLE 26

0.200 g (.45 mmole) of the all cis-3-carbethoxyamino-4-carbo-p-menth-3-yloxyamino-2-tetrahydrothiophenevaleric acid, prepared in Example 25, was dissolved in a mixture of 1.5 ml of 1N sodium hydroxide and 0.0 ml of water. The system was refluxed for 5.0 hrs. Upon cooling, some menthol was deposited. The reaction mixture was partitioned between 10 ml of 1N sodium hydroxide and 20 ml of methylene chloride. After an additional two 10 ml extractions with dichloromethane, the aqueous layer was acidified with 1N HCl to pH 1. After filtration of an insoluble impurity, the filtrate was evaporated to dryness. The residue was suspended in 50 ml of dry methanol, treated with 2 drops of conc. sulfuric acid, and refluxed 0.45 hr. The mixture was then concentrated, and the residue was partitioned between 20 ml of methylene chloride and 50 ml of water. The aqueous layer was further extracted three times with 20 ml portions of methylene chloride. The organic phases were combined dried over sodium sulfate, and evaporated to yield 0.030 g (0.123 mmole, 27%) of biotin methyl ester. After recrystallization from methanol diethyl ether, a specimen of m.p. 128°–129° C. was obtained. $[\alpha]_D^{25} = -3.8°$, which corresponds to an optical induction of 5%, with an enantiomeric excess of 1-biotin.

We claim:

1. A compound of the formula:

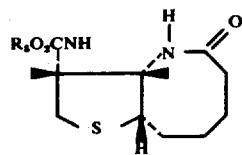

wherein $R_5$ is a straight or branched chain aliphatic hydrocarbyl group having from 1–20 carbon atoms; a cycloaliphatic group selected from the group consisting of menthyl, bornyl and cholesteryl and aryl lower alkyl groups wherein the aryl moiety is selected from the group consisting of phenyl, tolyl, naphthyl, phenanthryl and azulyl wherein said aryl moieties may be unsubstituted or substituted with lower alkylenedioxy, halogen, lower alkyl, lower alkoxy or a nitro group and the lower alkyl moiety is a straight or branched chain alkyl group having 1 to 8 carbon atoms.

2. The compound of claim 1 wherein said compound is all cis-d,1-3-amino-4-carbomethoxyamino-2-tetrahydrothiophenevaleric acid lactam.

* * * * *